US012734137B2

(12) United States Patent
Farr et al.

(10) Patent No.: US 12,734,137 B2

(45) **Date of Patent: *Sep. 15, 2026**

(54) METHODS OF TREATING LENNOX-GASTAUT SYNDROME USING FENFLURAMINE

(71) Applicant: ZOGENIX INTERNATIONAL LIMITED, Berkshire (GB)

(72) Inventors: Stephen J. Farr, Orinda, CA (US); Bradley S. Galer, West Chester, PA (US)

(73) Assignee: ZOGENIX INTERNATIONAL LIMITED, Berkshire (GB)

(*) Notice: Subject to any disclaimer, the term of this patent is extended or adjusted under 35 U.S.C. 154(b) by 423 days.

This patent is subject to a terminal disclaimer.

(21) Appl. No.: 16/864,955

(22) Filed: May 1, 2020

(65) Prior Publication Data

US 2020/0253895 A1 Aug. 13, 2020

Related U.S. Application Data

(63) Continuation of application No. 15/246,346, filed on Aug. 24, 2016, now abandoned.

(60) Provisional application No. 62/209,090, filed on Aug. 24, 2015.

(51) Int. Cl.

| | |
|---|---|
| ***A61K 31/137*** | (2006.01) |
| ***A61K 9/00*** | (2006.01) |
| ***A61K 9/08*** | (2006.01) |
| ***A61K 9/70*** | (2006.01) |
| ***A61K 31/19*** | (2006.01) |
| ***A61K 31/351*** | (2006.01) |
| ***A61K 31/357*** | (2006.01) |
| ***A61K 31/551*** | (2006.01) |
| ***A61K 45/06*** | (2006.01) |
| ***A61P 25/08*** | (2006.01) |

(52) U.S. Cl.

CPC .......... *A61K 31/137* (2013.01); *A61K 9/0053* (2013.01); *A61K 9/7023* (2013.01); *A61K 31/19* (2013.01); *A61K 31/357* (2013.01); *A61K 31/551* (2013.01); *A61K 45/06* (2013.01); *A61P 25/08* (2018.01); *A61K 9/0095* (2013.01); *A61K 9/08* (2013.01)

(58) Field of Classification Search

CPC ................ A61K 31/137; A61K 9/0053; A61K 9/7023; A61K 31/19; A61K 31/357; A61K 31/551; A61K 45/06; A61K 9/0095; A61K 9/08; A61P 25/08

See application file for complete search history.

(56) References Cited

U.S. PATENT DOCUMENTS

| | | | |
|---|---|---|---|
| 3,117,160 | A | 1/1964 | Holland |
| 3,198,833 | A | 8/1965 | Beregi |
| 3,198,834 | A | 8/1965 | Beregi et al. |
| 3,759,979 | A | 9/1973 | Beregi et al. |
| 4,452,815 | A | 6/1984 | Wurtman |
| 4,824,987 | A | 4/1989 | Kleeman |
| 4,857,553 | A | 8/1989 | Ward et al. |
| 5,587,398 | A | 12/1996 | Elmaleh et al. |
| 5,808,156 | A | 9/1998 | Cannata et al. |
| 5,811,586 | A | 9/1998 | Cannata et al. |
| 5,834,477 | A | 11/1998 | Mioduszewski |
| 5,985,880 | A | 11/1999 | Chang |
| 6,045,501 | A | 4/2000 | Elsayed et al. |
| 6,315,720 | B1 | 11/2001 | Williams et al. |
| 6,561,976 | B2 | 5/2003 | Elsayed et al. |
| 6,561,977 | B2 | 5/2003 | Williams et al. |
| 6,599,901 | B1 | 7/2003 | Flohr |
| 6,755,784 | B2 | 6/2004 | Williams et al. |
| 6,869,399 | B2 | 3/2005 | Williams et al. |
| 6,908,432 | B2 | 6/2005 | Elsayed et al. |
| 7,141,018 | B2 | 11/2006 | Williams et al. |
| 7,585,493 | B2 | 9/2009 | Hale |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,874,984 | B2 | 1/2011 | Elsayed et al. |
| 7,895,059 | B2 | 2/2011 | Reardan et al. |
| 7,959,566 | B2 | 6/2011 | Williams et al. |
| 8,204,763 | B2 | 6/2012 | Elsayed et al. |
| 8,263,650 | B2 | 9/2012 | Cook et al. |
| 8,315,886 | B2 | 11/2012 | Williams et al. |

(Continued)

FOREIGN PATENT DOCUMENTS

| | | |
|---|---|---|
| CN | 1425167 | 6/2003 |
| CN | 103025301 | 4/2013 |

(Continued)

OTHER PUBLICATIONS

NCT03936777 (Year: 2019).*
Russo (Year: 2006).*
Lazarova et al (Abstract) (Year: 1983).*
Porter (Year: 2013).*
Russo (Year: 2005).*
Lazarova (Abstract) (Year: 1983).*
Gastaut (Year: 1987).*
Camfield (Year: 2011).*
Ceulemans (Year: 2012).*

(Continued)

*Primary Examiner* — Jeffrey S Lundgren
*Assistant Examiner* — Ibrahim D Bori
(74) *Attorney, Agent, or Firm* — Sterne, Kessler, Goldstein & Fox P.L.L.C.

(57) ABSTRACT

A method of treating and/or preventing symptoms of Lennox-Gastaut Syndrome (LGS) also known as Lennox Syndrome in a patient such as a patient previously diagnosed with Lennox Syndrome, by administering an effective dose of fenfluramine or its pharmaceutically acceptable salt to that patient. Lennox Syndrome patients are treated at a preferred dose of less than about 2.0 to about 0.01 mg/kg/day.

20 Claims, 2 Drawing Sheets

(56) References Cited

U.S. PATENT DOCUMENTS 8,386,274 B1 2/2013 Pinsonneault
8,457,988 B1 6/2013 Reardan et al.
8,589,182 B1 11/2013 Reardan et al.
8,589,188 B2 11/2013 Elsayed et al.
8,626,531 B2 1/2014 Williams et al.
8,731,963 B1 5/2014 Reardan et al.
9,125,900 B2 9/2015 Meyer
9,549,909 B2 1/2017 Ceulemens
9,603,814 B2 3/2017 Ceulemens
9,603,815 B2 3/2017 Ceulemens
9,610,260 B2 4/2017 Ceulemens
10,351,509 B2 7/2019 Londesbrough
10,351,510 B2 7/2019 Londesbrough
10,452,815 B2 10/2019 Stewart et al.
10,478,441 B2 11/2019 Ceulemens
10,478,442 B2 11/2019 Ceulemens
10,517,841 B1 12/2019 Galer et al.
10,603,290 B2 3/2020 Farr
10,682,317 B2 6/2020 Abu-Izza
10,689,324 B2 6/2020 Farr
10,947,183 B2 3/2021 Londesbrough et al.
10,950,331 B2 3/2021 Stewart et al.
10,952,976 B2 3/2021 Galer
11,040,018 B2 6/2021 Farr
11,634,377 B2 4/2023 Londesbrough et al.
11,949,918 B2 4/2024 Li et al.
2002/0038310 A1 3/2002 Reitberg
2003/0007934 A1 1/2003 Rabinowitz et al.
2003/0118654 A1 6/2003 B. Santos et al.
2004/0249212 A1 12/2004 Smallridge et al.
2005/0182103 A1 8/2005 Finke et al.
2006/0121066 A1 6/2006 Jaeger et al.
2006/0270611 A1 11/2006 Dries et al.
2008/0004904 A1 1/2008 Tran
2008/0103179 A1 5/2008 Tam
2008/0243584 A1 10/2008 Srinivasan
2008/0261962 A1 10/2008 Greer
2009/0171697 A1 7/2009 Glauser
2010/0088778 A1 4/2010 Mulley
2010/0298181 A1 11/2010 Hanada et al.
2011/0092535 A1 4/2011 Barnes et al.
2011/0212171 A1 9/2011 Venkatesh et al.
2011/0230473 A1 9/2011 Gordon et al.
2011/0263526 A1 10/2011 Satyam
2012/0065999 A1 3/2012 Takatoku
2012/0107396 A1 5/2012 Khan
2012/0115958 A1 5/2012 Mariotti et al.
2012/0157392 A1 6/2012 Martin et al.
2012/0270848 A1 10/2012 Mannion
2013/0218586 A1 8/2013 Huser
2013/0296398 A1 11/2013 Whalley
2014/0030343 A1 1/2014 Lamson
2014/0142140 A1 5/2014 Bird
2014/0162942 A1 6/2014 Ghosal
2014/0329908 A1 11/2014 Ceulemens et al.
2014/0343044 A1 11/2014 Ceulemens et al.
2014/0343162 A1* 11/2014 Ceulemens .......... A61K 31/137
514/654
2014/0348966 A1 11/2014 Balemba
2015/0080377 A1 3/2015 Dhanoa
2015/0291597 A1 10/2015 Mannion
2015/0310187 A1 10/2015 Rabinowitz
2015/0359755 A1 12/2015 Guy et al.
2016/0092652 A1 3/2016 Stewart et al.
2016/0136114 A1 5/2016 Ceulemens et al.
2016/0228454 A1 8/2016 Zhang et al.
2016/0249863 A1 9/2016 Ando
2016/0279159 A1 9/2016 Hirano et al.
2017/0020885 A1 1/2017 Hsu
2017/0056344 A1 3/2017 Farr
2017/0071940 A1 3/2017 Olaleye et al.
2017/0071949 A1 3/2017 De Witte et al.
2017/0151194 A1 6/2017 Ceulemens
2017/0151214 A1 6/2017 Ceulemens et al.
2017/0151257 A1 6/2017 Ceulemens
2017/0151259 A1 6/2017 Ceulemens
2017/0174613 A1 6/2017 Londesbrough et al.
2017/0348303 A1 12/2017 Bosse
2018/0028499 A1 2/2018 Baraban et al.
2018/0092864 A1 4/2018 Martin et al.
2018/0141953 A1 5/2018 Dax
2018/0148403 A1 5/2018 Londesbrough et al.
2018/0215701 A1 8/2018 Carroll et al.
2021/0158920 A1 5/2021 Stewart et al.
2023/0093150 A1 3/2023 Morrison et al.
2023/0165810 A1 6/2023 Galer et al.
2024/0238222 A1 7/2024 Farr et al.
2024/0245631 A1 7/2024 Farr et al.

FOREIGN PATENT DOCUMENTS

CN 103886415 6/2014
DE 2150399 4/1973
EP 0 441 160 8/1991
EP 0 920 864 6/1999
EP 1 399 015 1/2010
EP 2 399 513 12/2011
EP 3170807 5/2017
GB 1399015 6/1975
HU 204497 1/1992
JP A S64-066116 3/1989
JP H05-310564 A 11/1993
JP A-2008-536545 9/2008
JP A-2009-525977 7/2009
JP A 2010-520162 6/2010
JP A-2011-221623 11/2011
JP A-2011-529923 12/2011
JP A-2012-511969 5/2012
JP A-2012-520130 9/2012
JP A-2012-208669 10/2012
JP A-2013-536857 9/2013
JP A-2013-248329 12/2013
RU 2317104 2/2008
RU 103209 3/2011
RU 2503448 1/2014
RU 2571501 12/2015
WO WO 1995/04713 2/1995
WO WO 1995/32962 12/1995
WO WO 2001/86506 11/2001
WO WO 2003/026591 4/2003
WO WO 2003/077847 9/2003
WO WO 2005/004865 1/2005
WO WO 2006/100676 9/2006
WO WO 2007/073503 6/2007
WO WO 2007/092469 8/2007
WO WO 2008/025148 3/2008
WO WO 2008/104524 9/2008
WO WO 2009/087351 7/2009
WO WO 2010/015029 2/2010
WO WO 2010/020585 2/2010
WO WO 2010/025931 3/2010
WO WO 2010/075115 7/2010
WO WO 2010/104841 9/2010
WO WO 2010/121022 10/2010
WO WO 2011/112606 9/2011
WO WO 2011/146850 11/2011
WO WO 2012/030927 3/2012
WO WO 2013/096878 6/2013
WO WO 2013/122897 8/2013
WO WO 2014/177676 11/2014
WO WO 2015/026849 2/2015
WO WO-2015026849 A1 * 2/2015 .......... A61K 31/137
WO WO 2015/066344 5/2015
WO WO 2015/193668 12/2015
WO WO 2016/051271 4/2016
WO WO 2016/138138 9/2016
WO WO 2016/205671 12/2016
WO WO 2017/035267 3/2017
WO WO 2017/112702 6/2017
WO WO 2017/122701 6/2017
WO WO 2018/037306 3/2018
WO WO 2018/060732 4/2018
WO WO 2018/206924 11/2018
WO WO 2019/067405 4/2019

(56) References Cited

FOREIGN PATENT DOCUMENTS

| | | |
|---|---|---|
| WO | WO 2019/067413 | 4/2019 |
| WO | WO 2019/067419 | 4/2019 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |

OTHER PUBLICATIONS

Aras et al., "The European patient with Dravet Syndrome: Results from a parent-reported survey on antiepileptic drug use in the European population with Dravet Syndrome" Epilepsy & Behavior (2015) 44:104-109.
Clinical Trials ClinicalTrials.gov Identifier: NCT02224560 (Jul. 27, 2018).
Russo et al., "Agonistic Properties of Cannabidiol at 5-HT1a Receptors" Neurochemical Research (2005) 30(8):1037-1043.
Dravet, Charlotte, "The core Dravet syndrome phenotype" Epilepsia, 52(Supp. 2):3-9 (2011).
Selmer et al., "SCN1A mutation screening in adult patients with Lenox-Gastaut syndrome features" Epilepsy & Behavior (Nov. 1, 2009) 16(3):555-57.
Aicardi et al., "Treatment of Self-Induced Photosensitive Epilepsy with Fenfluramine" New England Journal of Medicine (1985) 313:1419.
Aicardi et al., "Syncopal Attacks Compulsively Self-induced by Valsalva's Maneuver Associated with Typical Absence Seizures" Archives of Neurology (1988) 45:923-925.
Bird et al., "Combination of pharmaceutical compositions for treatment of neurological disorders" STN International (Columbus, Ohio) HCAPLUS database, Accession No. 2013:83254 (2013).
Coma et al, "New combination therapies for treating neurological dissorders" STN International (Columbus, Ohio) HCAPLUS database, Accession No. 2013:682383 (2013).
Cozzi et al., "Indan Analogs of Fenfluramine and Norfenfluramine Have Reduced Neurtoxic Potential" Pharmacology Biochemistry and Behavior (1998) 59(3):709-715.
Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).
Droogmans et al., "Role of echocardiography in tox heart vavulopathy" European Journal of Echocardiography, 10:467-476 (2009).
Experimental Chemistry (Continued), Part 2, Separation and Purification, (Maruzen, Co., Ltd.), Jan. 25, 1967, pp. 159-162 and 184-193.
File History of U.S. Pat. No. 9,549,909 issued on Jan. 24, 2018 (571 pp).
File History of U.S. Pat. No. 9,603,815 issued on Mar. 28, 2017 (385 pp).
File History of U.S. Pat. No. 9,603,814 issued on Mar. 28, 2017 (466 pp).
File History of U.S. Pat. No. 9,610,260 issued on Apr. 4, 2017 (371 pp).
File History of U.S. Pat. No. 10,478,441 issued on Nov. 19, 2019 (761 pp).
File History of U.S. Pat. No. 10,478,442 issued on Nov. 19, 2019 (980 pp).
File History of U.S. Appl. No. 14/447,369, filed Jul. 30, 2014 (now abandoned) (285 pp.).
File History of U.S. Appl. No. 15/429,650, filed Feb. 10, 2017 (now abandoned) (267 pp).
File History of U.S. Appl. No. 15/429,641, filed Feb. 10, 2017 (now abandoned) (285 pp).
File History of U.S. Appl. No. 15/429,506, filed Feb. 10, 2017 (now abandoned) (641 pp).
File History of U.S. Appl. No. 16/596,166, filed Oct. 8, 2019 (now abandoned) (123 pp).
File History of U.S. Appl. No. 16/869,284, filed May 7, 2020 (now abandoned) (42 pp).
File History of U.S. Appl. No. 16/909,055, filed Jun. 12, 2020 (pending) (85 pp).
File History of U.S. Pat. No. 10,351,509 issued Jul. 16, 2019 (226 pp).
File History of U.S. Pat. No. 10,351,510 issued Jul. 16, 2019 (244 pp).
File History of U.S. Pat. No. 10,947,183 issued Mar. 16, 2021 (293 pp).
Garone et al., "Deoxypyrimidine monophosphate bypass therapy for thymidine kinase 2 deficiency" EMBO Molecular Medicine Aug. 1, 2014) 6(8):1016-1027.
Gross et al., "The influence of the sparteine/debrisoquine genetic polymorphism on the disposition of dexfenfluramine" Br J Clin Pharmacol (1996) 41:311-317.
Hattori et al., "A Screening test for the prediction of Dravet Syndrome before one year of age" Epilepsia (Apr. 2008) 49(4):626-633.
Hawkins et al., "Synthesis of [14C] Fenfluramine and [14C]-S780" Journal of Labelled Compounds (1974) 10(4):63-670.
Hirayama, Noriaki, Organic Compound Crystallization Handbook: Principles and Know-How (Maruzen, Co., Ltd.), Jul. 25, 2008, pp. 57-84.
Ji et al., "Study of Fenfluramine Synthesis Route" Journal of Shenyang College of Pharmacy (Apr. 1994) 11(2):116-118.
Kaiser et al., "Synthesis and Anorectic Activity o Some 1-Benzylcyclopropylamines" Journal of Medicinal Chemistry, American Chemical Society, US (1970) 13(5):820-826.
Lambert et al., "Inductive Enhancement of Aryl Participation" Journal of the American Chemical Society (Apr. 27, 1977) 99(9):3059-67.
Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.
LoPinto-Khoury et al., "Antiepileptic Drugs and Markers of Vascular Risk" Curr Treat Options Neurol (Jul. 2010) 12(4):300-308.
Notification issued by the Director of Pharmaceutical and Medical Safety Bureau, Ministry of Health and Welfare, Guidelines for Residual Solvents in Pharmaceuticals, PMSB/ELD Notification No. 307, 1998, pp. 1-11.
Patani et al.;, "Bioisosterism: A Rational Approach to Drug Design" Chem. Rev. (1996) 96:3147-3176.
Porra et al., "Determination of Fenfluramine Enantiomers in Pharmaceutical Formulations by Capillary Zone Electrophoresis" Chromatographia (Oct. 1995) 41(7/8):383-388.
Pottkamper et al., "The postictal state—What do we know?" Epilepsia (2020) 61(6):1045-1061.
Registry(STN) [online], Jun. 7, 2015, [Retrieval Date: Sep. 28, 2020], CAS Registry No. 1775169-27-1.
Remi et al., "Clinical features of the postictal state: Correlation with seizure variables" Epilepsy & Behavior (2010) 91(2):114-117.
Su et al, "The Synthesis of 2-Amino-1-Penylpropanes" Chemical Journal of Chinese Universities (1988) 9(2):134-139.
Subota et al., "Signs and Symptoms of the postictal period in epilepsy: A systematic review and meta-analysis" Epilepsy & Behavior (2019) 94:243-251.
Thurman et al., "Sudden expected death in epilepsy: Assessing the public health burden" Epilepsia (2014) 55(10):1479-1485.
Tupal et al., "Serotonin 5-$HT_4$ receptors play a critical role in the action of fenfluramine to block seizure-induced sudden death in a mouse model of SUDEP" Epilepsy Research (2021) 177:1-7.
Van Der Steldt et al., "The Effect of Alkyl Substitution in Drugs" Arzneimittelforschung—Drug Research (1965) 15:1251-1253.
Vivero et al., "A close look at fenfluramine and dexfenfluramine" The Journal of Emergency Medicine (1998) 16(2):197-205.
Werbel et al., "Synthesis, Antimalarial Activity, and Quantitative Structure-Activity Relationships of Tebuquine and a Series of

(56) References Cited

OTHER PUBLICATIONS

Related 5-[(7-Chloro-4-quinolinyl)amino]-3[(alkylamino)methyl][1,1'-biphenyl]-2-ols and N omega-Oxides" J. Med. Chem. (1986) 29:924-939.

Bagdy et al., "Serotonin and epilepsy," J. Neurochem., 100:857-73 (2007).

Ceulemans et al., "Clinical Correlations of Mutations in the SCN1A Gene: From Febrile Seizures to Severe Myoclonic Epilepsy in Infancy" Pediatr. Neurol. 30(4):236-43 (2004).

Coleman et al., "Monitoring for adverse drug reactions," Br. J. Clin. Pharmacol., 61(4):371-78 (2006).

"Diacomit: EPAR—Scientific Discussion," European Medicines Agency ("EPAR Diacomit") https://www/ema/europa.eu/en/documents/scientific-discussion/diacomit-epar-scientific-discussion_en.pdf, published 2009.

Ferretti et al., "Direct High-performance liquid chromatograph resolution on a chiral column of dexfenfluramine and its impurities, in bulk raw drug and pharmaceutical formulations" J. Chromatogr. A. 731:340-45 (1996).

Gordon et al., "A SARS-CoV-2 protection interaction map reveals targets for drug repurposing" Nature (Apr. 30, 2020) 583(7816:459-468.

Haute Autorité de Santé (HAS), French National Authority for Health, issued an opinion on Diacomit ("HAS Opinion") https://www.has-sante.fr/upload/dox/application/pdf/2010-01/diacomit_ct_4347.pdf (Jun. 6, 2007).

Heisler et al., "Epilepsy and Obesity in Serotonin 5-$HT_{2C}$ Receptor Mutant Mice," Ann. NY Acad. Sci. 861:74-78 (1998).

International Conference On Harmonisation Of Technical Requirements for Registration of Pharmaceuticals for Human Use," ICH Harmonised Tripartite Guidline: Impurities in New Drug Substances," Q3A(R2) (2006).

Jingyu et al., "Study on Synthesis of Amphetamine Compounds" Chem J. of Chinese Univ., 9(2), 12 pages (1988).

Martin et al., "Fenfluramine acts as a positive modulator of sigma-1 receptors" Epilepsy and Behavior, Academic Press, San Diego, CA, US (Mar. 10, 2020) 105:1-9.

Mathews et al., "Effect of D-Fenfluramine on the Lymphocyte Response of HIV+ Humans" International Journal of Immunopharmacology (Jan. 1, 1998) 20:751-763.

Olson et al., "Cyclin-Dependent Kinase-Like 5 Deficiency Disorder: Clinical Review" Pediatric Neurology (2019) 97:18-25.

Public Law 110-85, 110th Congress ("FDA Amendments Act of 2007") published 2007.

Rothman et al., "(+)-Fenfluramine and Its Major Metabolite, (+)-Norfenfluramine, Are Potent Substrates for Norepinephrine Transporters," J. Pharmacol. Exp. Ther., 305(3):1191-99 (2003).

Scala et al., "CDKL5/STK9 is mutated in Rett syndrome variant with infantile spasms" J Med Genet (2005) 42:103-107.

Tran et al., "Dakin-West Synthesis of β-Aryl Ketones" J. Org. Chem. (2006) 71:6640-6643.

Vela, Jose Miguel "Repurposing Sigma-1 Receptor Ligands for COVID-19 Therapy?" Frontiers in Pharmacology (Nov. 9, 2020) 11:1-23.

Wee et al., "Risk for Valvular Heart Disease among Users of Fenfluramine and Dexfenfluramine Who Underwent Echocardiography before Use of Medication," Annals of Internal Medicine, 129(11):870-874 (1998).

Klein et al., "Cannabidiol potentiates Delta9-tetrahydrocannabinol (THC) behavioural effects and alters THC pharmacokinetics during acute and chronic treatment in adolescent rats" Psychopharmacology (2011) 218:443-457.

Slick et al., "Frequency of Scale Elevations and Factor Structure of the Behavior Rating Inventory of Executive Function (Brief) in Children and Adolescents with Intractiable Epilepsy" Child Neuropsychology (2006) 12:181-189.

Anonymous, "Health Technology Briefing: Fenfluramine hydrochloride for treatment of seizures associated with Lennox-Gastaut syndrome" NIHR Innovation Observatory (May 2019) 8 pages.

Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.

Baker, M. "Zogenix Completes Enrollment in Phase 3 Trial of FINTELPLA in Lennox-Gastaut Syndrome" (Jul. 8, 2019) 2 pages.

ONFI Prescribing Information. Lundbeck, Deerfield, Reference ID: 4028780 [online], Dec. 2016, [retrieved on Jun. 22, 2021, <URL: https://www.accessdata.fda.gov/drugsatfda_docs/label/2016/203993s005lbl.pdf>.

Study NCT02926898 on Date: May 1, 2017 (v6), ClinicalTrials.gov archive[online], May 1, 2017, [retrieved on Jun. 22, 2021], <URL: https://clinicaltrials.gov/ct2/history/NCT02926898>.

Zaccara et al., "Interactions between antiepileptic drugs, and between antiepileptic drugs and other drugs" Seminar in Epileptology (2014) 16(4): 409-432.

Inoue et al., "Stiripentol open study in Japanese patients with Dravet Syndrome" Epilepsia, 50(11):2362-2368 (2009).

Van Rijckevorsel, Kenou, "Treatment of Lennox-Gastaut syndrome: overview and recent findings" Neuropsychiatric Disease and Treatment, 4(6):1001-1019 (2008).

Kelley et al., "Doose syndrome (myoclonic-astatic epilepsy): 40 years of progress" Developmental Medicine & Child Neurology (2010) 52(11):988-993.

McTague et al., "The genetic landscape of the epileptic encephalopathies of infancy and childhood" Lancet Neurol. (2016) 15:304-316.

Oguni et al., "Treatment and Long-Term Prognosis of Myoclonic-Astatic Epilepsy of Early Childhood ," Neuropediatrics (2002) 33(3):122-32.

Anandam, R., Affiliations Indian Journal of Pediatrics (Jan. 1, 2000) 67 (1 Suppl):S88-91 (Abstract Only).

Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness", Federal Register, (Sep. 29, 2015).

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).

Arzimanoglou, "Dravet syndrome: From electroclinical characteristics to molecular biology" Epilepsia, 50(Suppl. 8):3-9 (2009).

Boel and Casaer, "Add-on Therapy of Fenfluramine in Intractable Self-Induced Epilepsy" Neuropaediatrics 1996, 27(4):171-173.

F Brenot et al., "Primary Pulmonary Hypertension and Fenfluramine Use.", Heart, vol. 70, No. 6, Dec. 1, 1993 (Dec. 1, 1993), pp. 537-541.

Brunklaus et al., "Prognostic, clinical and demographic features in SCN1A mutation-positive Dravet syndrome" Brain, 2012, p. 1-8.

Brunklaus et al., "Dravet syndrome-From epileptic encephalopathy to channelopathy" Epilepsia (May 16, 2014) 55(7):979-984.

Buchanan, Gordon F. et al., Serotonin neurones have anti-convulsant effects and reduce seizure-induced mortality, The Journal of Physiology, 2014, vol. 592, Issue 19, p. 4395-4410.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. B. Catarino et al. "Dravet Syndrome as epileptic encephalopathy: Evidence from long-term course and neuropathology", Brain, vol. 134, No. 10 (Jun. 29, 2011) pp. 2982-3010.

Ceulemans et al., "Poster presented at the $69^{th}$ Annual Meeting of the American Epilepsy Society" (Dec. 2015) Philadelphia.

Ceulemans et al., "Successful use of fenfluramine as an add-on treatment for Dravet syndrome" Epilepsia, 53(7), 2012, 1131-1139.

Ceulemans, "Overall management of patients with Dravet syndrome" Developmental Medicine & Child Neurology, 2011, 53, 19-23.

(56) References Cited

OTHER PUBLICATIONS

Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).
Ceulemans B., "Successful Use of Fenfluramine as Add-On Treatment in Dravet Syndrome" Epilepsia, 52(Suppl. 6):4-22 (2011).
Ceulemans et al., "Five-year extended follow-up status of 10 patients with Dravet syndrome treated with fenfluramine" Epilepsia (May 20, 2016) 57(7):e129-e134.
Chiron et. al., "The pharmacologic treatment of Dravet syndrome" Epilepsia (2011) 52(Suppl 2):72-75.
Clemens B., "Dopamine agonist treatment of self-induced pattern-sensitive epilepsy. A case Report" Epilepsy Res. 2. 1988, p. 340-343.
Curzon et al., "Appetite suppression by commonly used drugs depends on 5-HT receptors but not on 5-HT availability" Tips (1997) 18:21-25.
Devinsky et al., "Trial of Cannabidiol for Drug-Resistant Seizures in the Dravet Syndrome" The New Engalnd Journal of Medicine (May 25, 2017) 376(21):2011-2020.
C. Doege et al., "Myoclonic-astatic epilepsy: Doose-Syndrum 2014: Doose syndrome 2014", Zeitschrift FR Epileptologie, (Mar. 20, 2014).
Döring et al. "Thirty Years of Orphan Drug Legislation and the Development of Drugs to Treat Rare Seizure Conditions: A Cross Sectional Analysis" PLOS One, pp. 1-15 (Aug. 24, 2016).
Faingold et al., "Prevention of seizure-induced sudden death in a chronic SUDEP model by semichronic administration of a selective serotonin reuptake inhibitor" Epilepsy & Behavior (2011) 22:186-190.
Favale et al., "The anticonvulsant effect of citalopram as indirect evidence of serotonergic impairment in human epileptogenesis" Seizure (2003) 12:316-319.
Franco-Perez, Javier "The Selective Serotonin Reuptake Inhibitors: Antidepressants with Anticonvulsant Effects?" Ann Deoress Anxiety (2014) 1(5):1025 (2 pages).
Gastaut et al., "Compulsive respiratory sterotypies in children with autistic features: Polygraphic recording and treatment with fenfluramine" Journal of Autism and Developmental Disorders, (Sep. 1, 1987) 17(3):391-406.
K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.
Gharedaghi et al., "The role of different serotonin receptor subtypes in seizure susceptibility" Exp. Brain Res (2014) 232:347-367.
Gioia et al., "Confirmatory Factor Analysis of the Behavior Rating Inventory of Executive Function (BRIEF) in a Clinical Sample" Child Neuropsychology (2002) 8(4):249-57.
Habibi et al., "The Impact of Psychoactive Drugs on Seizures and Antiepileptic Drugs" Current Neurology and Neuroscience Reports (Jun. 17, 2016) 16(8):1-10.
Haritos et al., "Metabolism of dexfenfluramine in human liver microsomes and by recombinant enzymes: Role of CYP2D6 and 1A2" Pharmcogenetics (Oct. 1998) 8(5):423-432.
Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).
Hazai et al., "Reduction of toxic metabolite formation of acetaminophen" Biochemical and Biophysical Research Communications (Mar. 8, 2002) 291(4):1089-1094.
Hegadoren et al., "Interactions of iprindole with fenfluramine metabolism in rat brain and liver" Journal of Psychiatry & Neuroscience (Mar. 1991) pp. 5-11.
Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.
Katholieke Universiteit Leuven, University Hospital Antwerp: "Interim results of a fenfluramine open-label extension study", European Patent Register (May 25, 2017).
Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.
Lagae et al. "A pilot, open-label study of the effectiveness and tolerability of low-dose ZX008 (fenfluramine HC1) in Lennox-Gastaut syndrome" Epilepsia (2018) 59: 1881-1888.
Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.
LeJeune et al., "Psychometric Support for an Abbreviated Version of the Behavior Rating Inventory of Executive Function (BRIEF) Parent Form" Child Neuropsychology (2010 16:182-201.
Lopez-Meraz et al., "5-$HT_{1A}$ receptor agonist modify epileptic seizures in three experimental models in rats" Neuropharmacology (2005) 49:367-375.
Manzke et al., "5-HT4(a) receptors avert opiod-induced breathing depression without loss of analgesia" Science (Jul. 11, 2003) 301:226-229.
Martin, et al., "An Examination of the Mechanism of Action of Fenfluramine in Dravet Syndrome: A Look Beyond Serotonin" Presented as part of the Zogenix Scientific Exhibit During the $70^{th}$ Annual Meeting of the American Epilepsy Society, Houston, Texas (Dec. 2-6, 2016).
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Mudigoudar et al., "Emerging Antiepileptic Drugs for Severe Pediatric Epilepsies" Seminars in Pediatric Neurology (Jun. 2016) 23(2):167-179.
Mulley et al., "SCN1A Mutations and Epilepsy" Human Mutation (2005) 25:535-542.
Naithani et al., "The Conventional Antiepileptic Drug Use When Compared to a Combination Therapy Regime in a Teaching Hospital in India" International Journal of Pharma and Bio Sciences (2012) 3(1):B-191-B-197.
NCT02682927 (Sep. 3, 2016, 10 pages) Accessed from https://www.clinicaltrials.gov/ct2/history/NCT02682927?V_=View#StudyPageTop on Mar. 18, 2019).
Nozulak et al., "(+)-cis-4,5,7a,8,9,10,11,11a-Octahydro-7H-10-methylindolo[1,7-bc][2,6]-naphthridine: A 5-$HT_{2C/2B}$ Receptor Antagonist with Low 5-$HT_{2A}$ Receptor Affinity" J. Med. Chem. (1995) 38:28-33.
O'Neill et al., "GR46611 potentiates 5-$HT_{1A}$ receptor-mediated locomotor activity in the guinea pig" European Journal of Pharmacology (1999) 370:85-92.
Pirincci et al., "The Effects of Fefluramine on Blood and Tissue Seratonin (5-Hydroxytryptamine) Levels in Rats" Turk J Vet Anim Sci (2005) 29:857-863.
Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.
Jake Remaly: "Fenfluramine Reduces Convulsive Seizure Frequency in Dravet Syndrome. Epilepsy Resource Center", Jan. 1, 2018 (Jan. 1, 2018).
Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl. 5):5-11.
Rothman et al., "Serotonergic drugs and valvular heart disease" Expert Opinion on Drug Safety (May 2009) 8(3):317-329.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.

(56) References Cited

OTHER PUBLICATIONS

An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Sharma et al. Indian Journal of Pharmacology, 1996, 28(1), 1-10.
Sourbron et al., "Serotonergic Modulation as Effective Treatment for Dravet Syndrome in Zebrafish Mutant Model" ACS Chemical Neuroscience (Feb. 17, 2016) 7(5):588-598.
Sullivan et al. "Effext of ZX008 (fenfluramine HC1 oral solution) on total seizures in Dravet syndrome" Neurology: Official Journal of the American Academy of Neurology, 2018, 90(24):e2187-e2811.
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.
Wallace et al., "Pharmacotherapy for Dravet Syndrome" Paediatr. Drugs, 18(3):197-208 (Jun. 2016).
Wirrell et al., "Stiripentol in Dravet syndrome: Results of a retrospective U.S. study" Epilepsia (2013) 54(9):1595-1604.
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Wirrell et al., "Optimizing the Diagnosis and Management of Dravet Syndrome: Recommendations From a North American Consensus Panel" Pediatric Neurology (Mar. 2017) 68:18-34.
Wurtman et al., "Fenfluramine and other serotoninergic drugs depress food intake and carbohydrate consumption while sparing protein consumption" Current Medical Research and Opinion (1979) 6(1 Supp):28-33.
Yamaori et al., "Potent inhibition of human cytochrome P450 3A isoforms by cannabidiol: Role of phenolic hydroxyl groups in the resorcinol moiety" Life Sciences (2011) 88:730-736.
Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.
Zhang et al., *A Physiological-based Pharmacokinetic* (*PBPK*) *Modeling Approach to Quantifying Drug-Drug Interactions: Applications to the Development of Fenfluramine* (*ZX008*) *for Treatment of Seizures in Dravet Syndrome* (*DS*). Presented at the 2016 American Conference for Pharmacokinetics.
Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).
Zhang et al., "Pharmacological Characterization of an Antisense Knockdown Zebrafish Model of Dravet Syndrome: Inhibition of Epileptic Seizures by the Serotonin Agonist Fenfluramine" PLOS One (May 12, 2015) 10(5)::16-17 (Abstract).
Zhuang et al. (2016), "PBPK modeling and simulation in drug research and development" in Acta Pharmaceutica Sinica B 2016;6(5):430-440.
Zogenix "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].
Bih, C.I., et al., "Molecular Targets of Cannabidiol in Neurological Disorders," Neurotherapeutics 12(4):699-730, Springer Science, Germany (published online Aug. 12, 2015).
Catterall, W.A., et al., "Nav1.1 channels and epilepsy," J Physiol 588(Pt 11):1849-1859, The Physiological Society, United Kingdom (published online Mar. 1, 2010).
NCT0442295, "An Open-Label Study to Investigate the Safety of Single and Multiple Ascending Doses in Children and Adolescents with Dravet Syndrome," (first posted Jun. 22, 2020), accessed at https://clinicaltrials.gov/ct2/show/record/NCT04442295, on Mar. 27, 2023, 10 pages.
Fintepla, "Highlights of Prescribing Information," Fintepla (fenfluramine) oral solution, CIV, Revised: Jun. 2020, 33 pages.
Graf, M., et al., "Selective 5-$HT_{1A}$ and 5-$HT_7$ antagonists decrease epileptic activity in the WAG/Rij rat model of absence epilepsy," Neurosci. Lett. 359(1-2):45-48, Elsevier, Netherlands (Apr. 2004).
Guerrini, R., "Dravet syndrome: the main issues," Eur. J. Paediatr. Neurol. 16:S1-S4, Elsevier, Netherlands (Sep. 2012).
Guiard, B.P., and Di Giovanni, G., "Central serotonin-2A (5-HT2A) receptor dysfunction in depression and epilepsy: the missing link?" Front. Pharmacol. 6:46, Frontiers Media S.A., Switzerland (Mar. 2015).
Hancock, E.C., and Cross, J.H., "Treatment of Lennox-Gastaut syndrome," Cochrane Database Syst. Rev. 2013(2):CD003277, Wiley, United States (Feb. 2013).
Horn, C.S., et al., "Carbamazepine-exacerbated epilepsy in children and adolescents," Pediatr. Neurol. 2(6):340-345, Elsevier, Netherlands (Nov.-Dec. 1986).
Hsiao, J., et al., "Upregulation of Haploinsufficient Gene Expression in the Brain by Targeting a Long Non-coding RNA Improves Seizure Phenotype in a Model of Dravet Syndrome," EBioMedicine 9:257-277, Elsevier, Netherlands (Jul. 2016).
Knupp, K.G., et al., "Efficacy and Safety of Fenfluramine for the Treatment of Seizures Associated With Lennox-Gastaut Syndrome: A Randomized Clinical Trial," JAMA Neurol. 79(6):554-564, American Medical Association, United States (Jun. 2022).
Marini, C., et al., "The genetics of Dravet syndrome," Epilepsia 52(Suppl. 2):24-29, Wiley, United States (Apr. 2011).
Verrotti, A., et al., "The pharmacological management of Lennox-Gastaut syndrome and critical literature review," Seizure: European J. of Epilepsy 63:17-25, Elsevier, Netherlands (Dec. 2018).
Zuberi, S.M., et al., "Genotype-phenotype associations in SCN1A-related epilepsies," Neurology 76(7):594-600, Wolters Kluwer, Netherlands (Feb. 2011).
Fintepla Label, Highlights of Prescribing Information, Mar. 2023, 40 pages.
Gray, R.A., et al., "The proposed mechanisms of action of CBD in epilepsy," Epileptic Disord. 22 (Suppl. 1):S10-S15, John Libby Eurotext, France (Jan. 2020).
Rosenberg, E.C., et al., "Cannabinoids and Epilepsy," Neurotherapeutics 12:747-768, The American Society for Experimental Neuro Therapeutics, Inc., United States (2015).
Arzimanoglou, A., et al., "Lennox-Gastaut syndrome: a consensus approach on diagnosis, assessment, management, and trial methodology," Lancet Neurol. 8:82-93, Elsevier, Netherlands (Jan. 2009).
Cross, J.H., et al., "Expert opinion on the management of Lennox-Gastaut Syndrome: Treatment algorithms and practical considerations," Front. Neurol. 8:505, Frontiers Media, Switzerland (Sep. 2017).
European Medicines Agency, "Guideline on clinical investigation of medicinal products in the treatment of epileptic disorders," European Medicines Agency, European Union, 17 pages (Jul. 22, 2010).
Fintepla, Annex I: Summary of Product Characteristics, European Medicines Agency, 43 pages (Aug. 1, 2021).
Hahn, C.D., et al., "A phase 2, randomized, double-blind, placebo-controlled study to evaluate the efficacy and safety of soticlestat as adjunctive therapy in pediatric patients with Dravet syndrome or Lennox-Gastaut syndrome (ELEKTRA)," Epilepsia 63:2671-2683, Wiley-Blackwell, United States (Oct. 2022).
Knupp, K.G., et al., "Fenfluramine provides clinically meaningful reduction in frequency of drop seizures in patients with Lennox-Gastaut syndrome: Interim analysis of an open-label extension study," Epilepsia 64:139-151, Wiley-Blackwell, United States (Jan. 2023).
Summary of Clinical Trial NCT02655198. Add-on Therapy With Low Dose Fenfluramine in Lennox Gastaut Epilepsy, ClinicalTrials.

(56) References Cited

OTHER PUBLICATIONS gov, accessed at https://clinicaltrials.gov/study/NCT02655198?term=NCT02655198&viewType=Table&rank=1, updated on Sep. 22, 2023, 6 pages.
Declaration of Dr. Joseph Sullivan filed in EP 3340971, filed May 5, 2025, 4 pages.
Notice of Opposition filed in EP 3340971, dated Nov. 19, 2024, 30 pages.
Reply to Article 94(3) EPC Communication filed in EP 16840062.0, dated Feb. 15, 2023, 4 pages.
Response to the Notice of Opposition filed in EP 3340971, dated May 6, 2025, 22 pages.
Smeets, E.E.J., et al., "Rett Syndrome," Molecular Syndromology 2:113-127, Karger Publishers, Switzerland (Apr. 2012).
Specchio, N., et al., "International league against epilepsy classification and definition of epilepsy syndromes with onset in childhood: Position paper by the ILAE task force on nosology and definitions," Epilepsia 63:1398-1442, Wiley-Blackwell, United States (Jun. 2022).
Office Action mailed Jun. 27, 2024, in U.S. Appl. No. 18/418,121, filed Jan. 19, 2024, 15 pages.
Office Action mailed Nov. 8, 2024, in U.S. Appl. No. 18/418,121, filed Jan. 19, 2024, 21 pages.
Office Action mailed Oct. 2, 2025, in U.S. Appl. No. 18/418,133, filed Jan. 19, 2024, 13 pages.
Nieto-Barrera, Abstract of "Características e indicaciones del topiramato," Rev. Neurol. 35 Suppl. 1:S88-S95 (Sep. 2002), 1 page.
H. Angus-Leppan, "Diagnosing epilepsy in neurology clinics: A prospective study," *Seizure* 17:431-436, Elsevier Ltd., Netherlands (2007).
Al-Baradie, R.S., "Dravet syndrome, what is new?," *Neurosciences* 18(1):11-17, Armed Forces Hospital, Saudi Arabia (2013).
Bourgeois, B., et al., "Lennox-Gastaut Syndrome: A Consensus Approach to Differential Diagnosis," *Epilepsia* 55 (Suppl. 4):4-9, Blackwell Science, United States (2014).
Conry, J.A., et al., "Clobazam in the Treatment of Lennox-Gastaut Syndrome," *Epilepsia* 50(5):1158-1166, Blackwell Science, United States (2009).
Gentsch, K., et al., "Fenfluramine blocks low-$Mg^{2+}$-induced epileptiform activity in rat entorhinal cortex," *Epilepsia* 41(8):925-928, Lippincott Williams & Wilkins, Inc., Baltimore, MD (2000).
Merriam-Webster's Medical Dictionary, "diagnosis" on p. 188 and "referral" on p. 642, Merriam-Webster, Inc., Springfield, MA (2006).
Office Action mailed Dec. 4, 2025, in U.S. Appl. No. 18/418,121, filed Jan. 19, 2024, 24 pages.
Response to Summons to Attend Oral Proceedings filed in EP 3340971, dated Dec. 24, 2025, 8 pages.
Response to Reply to Notice of Opposition filed in EP 3340971, dated Dec. 29, 2025, 10 pages.
Samanta, D., "Fenfluramine: A Review of Pharmacology, Clinical Efficacy, and Safety in Epilepsy," *Children* 9(8):1159, MDPI AG, Switzerland (Aug. 2022).
Xu, Y., et al., "Frequency of a false positive diagnosis of epilepsy: A systemic review of observational studies," *Seizure* 41:167-174, Elsevier, Ltd., Netherlands (2016).

* cited by examiner

Figure 1

Trial flowchart

| Procedure | Visit 1 | Visit 2 | Visit 3 | Visit 4 | Visit 5 | Visit 6 | Follow-up |
|---|---|---|---|---|---|---|---|
| Week No. | 0 | 4 | 8 | 12 | 16 | | |
| | Start prospective baseline | Start add-on | | | | End of Study | Every 3 months |
| Informed consent | X | | | | | | |
| Baseline demographics | X | | | | | | |
| Clinical diagnosis confirmation | X | | | | | | |
| Seizure counting (pre-baseline) | X | | | | | | |
| Current treatment continuation | X | X | X | X | X | X | X |
| Dispense fenfluramine | | X | X | X | X | X[2] | X |
| Seizure diary | | X | X | X | X | X | X |
| Pregnancy test in WOCBP | X | X | X | X | X | X | X |
| Adverse events | | X | X | X | X | X | X |
| Safety blood sample collection[1] | X | | | | | X | X[1] |
| AED blood levels[1] | X | | | | | X | X[1] |
| Cardiac evaluation[1] | X | | | | | X | X[1] |
| Sleep quality | X | X | X | X | X | X | X |
| Clinical global impression | X | X | X | X | X | X | X |
| | | | | | | | |

[1]At the discretion of the PI at visits 2-5, and during follow-up period.

[2]For those continuing in follow-up

Scheme for Dose Escalation

METHODS OF TREATING LENNOX-GASTAUT SYNDROME USING FENFLURAMINE

FIELD OF THE INVENTION

This invention relates generally to the field of methods of treatment and in particular, methods of treating human patients, and more particularly towards treating human patients diagnosed with Lennox-Gastaut Syndrome.

BACKGROUND OF THE INVENTION

This invention relates to the treatment of symptoms of Lennox-Gastaut Syndrome ("LGS," sometimes referred to as "Lennox Syndrome") using an amphetamine derivative, specifically fenfluramine.

Fenfluramine, i.e. 3-trifluoromethyl-N-ethylamphetamine is an amphetamine derivative having the structure:

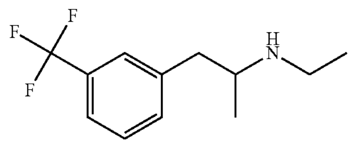

Systematic (IUPAC) name
(RS)-N-ethyl-
1-[3-(trifluoromethyl)phenyl]propan-
2-amine Fenfluramine was first marketed in the US in 1973 and had been administered in combination with phentermine to prevent and treat obesity. However, in 1997, it was withdrawn from the US and global market as its use was associated with the onset of cardiac valve fibrosis and pulmonary hypertension. Subsequently, the drug was withdrawn from sale globally and is no longer indicated for use in any therapeutic area. Without being bound by theory, the adverse effects associated with the use of fenfluramine as an anorexic agent are thought to be attributable to the interaction of fenfluramine's major metabolite norfenfluramine with the 5-HT2B receptor, which is associated with heart valve hypertrophy.

Fenfluramine is metabolized in vivo into norfenfluramine by cytochrome P450 enzymes in the liver. Cytochrome P450 enzymes such as CYP2D6 and CYP1A2 are primarily responsible for the production of norfenfluramine from fenfluramine in humans. Such metabolism includes cleavage of an N-ethyl group to produce norfenfluramine as shown below.

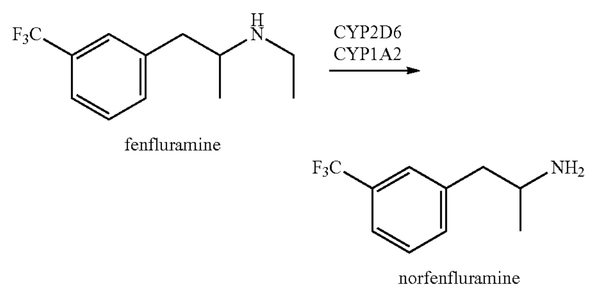

fenfluramine norfenfluramine

Despite past cardiovascular safety concerns that arose when high doses of fenfluramine were used for treatment of adult obesity, attempts have been made to identify further therapeutic uses for that product, while weighing the known cardiovascular risks of fenfluramine against potential therapeutic benefits. One disorder for which new treatment options are sorely needed is epilepsy, and in particular, epilepsy syndromes which are refractory to known treatments. Epilepsy is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident and alcohol withdrawal.

Prior to the inventor's work, investigation of fenfluramine's efficacy in epilepsy patients, while showing some initial promise, was far from definitive, and shared a common paradigm, i.e., that fenfluramine's primary effects were on behaviors that caused or induced seizures, not treating or preventing the seizure itself.

For example, Aicardi and Gastaut (New England Journal of Medicine (1985), 313:1419 and Archives of Neurology (1988) 45:923-925) reported four cases of self-induced photosensitive seizures, i.e., seizures caused by patients purposely staring into bright lights or the sun, that responded to treatment with fenfluramine.

Clemens, in Epilepsy Research (1988) 2:340-343 reported a case study wherein a boy suffering pattern sensitivity-induced seizures that were resistant to anticonvulsive treatment was treated with fenfluramine to curb the patient's compulsive seizure-inducing behavior. Fenfluramine reportedly successfully terminated these self-induced seizures and the author concluded that this was because fenfluramine blocked the seizure-sensitive triggering mechanism, i.e., not by treating the seizure itself.

In Neuropaediatrics, (1996); 27(4):171-173, Boel and Casaer reported on a study on the effects of fenfluramine on children with refractory epilepsy, all of whom exhibited compulsive seizure-inducing behavior. They observed that when fenfluramine was administered at a dose of 0.5 to 1 mg/kg/day, this resulted in a reduction in the number of seizures experienced by the patients, and concluded that "this drug could have significant anti-epileptic activity in a selected group of young patients with idiopathy or symptomatic generalized epilepsy, namely, children with self-induced seizures." The authors noted that "[i]t may well be that fenfluramine has no direct antiepileptic activity but acts through its effect on the compulsion to induce seizures." Hence the authors seemed to suggest that fenfluramine affected behavior and not the seizure itself.

In a letter to Epilepsia, published in that journal (Epilepsia, 43(2):205-206, 2002), Boel and Casaer commented that fenfluramine appeared to be of therapeutic benefit in patients with intractable epilepsy and self-induced seizures. However, the authors did not attribute fenfluramine's efficacy to generalized anti-seizure activity.

A large number of subtypes of epilepsy have been characterized, each with its own unique clinical symptoms, signs, and phenotype, underlying pathophysiology and distinct responses to different treatments. The most recent version, and the one that is widely accepted in the art, is that adopted by the International League Against Epilepsy's ("ILAE") Commission on Classification and Terminology [See e.g., Berg et al., "Revised terminology and concepts for organization of seizures," *Epilepsia,* 51(4):676-685 (2010)]:

I. ELECTROCHEMICAL SYNDROMES (arranged by age of onset):

A. Neonatal period

1. Benign familial neonatal epilepsy (BFNE)
2. Early myoclonic encephalopathy (EME)
3. Ohtahara syndrome B. Infancy 1. Epilepsy of infancy with migrating focal seizures
2. West syndrome
3. Myoclonic epilepsy in infancy (MEI)
4. Benign infantile epilepsy
5. Benign familial infantile epilepsy
6. Dravet syndrome
7. Myoclonic encephalopathy in non-progressive disorders C. Childhood 1. Febrile seizures plus (FS+) (can start in infancy)
2. Panayiotopoulos syndrome
3. Epilepsy with myoclonic atonic (previously astatic) seizures
4. Benign epilepsy with centrotemporal spikes (BECTS)
5. Autosomal-dominant nocturnal frontal lobe epilepsy (ADNFLE)
6. Late onset childhood occipital epilepsy (Gastaut type)
7. Epilepsy with myoclonic absences
8. Lennox-Gastaut syndrome
9. Epileptic encephalopathy with continuous spike-and-wave during sleep (CSWS), also known as Electrical Status Epilepticus during Slow Sleep (ESES)

10. Landau-Kleffner syndrome (LKS)
11. Childhood absence epilepsy (CAE)

D. Adolescence—Adult

1. Juvenile absence epilepsy (JAE)
2. Juvenile myoclonic epilepsy (JME)
3. Epilepsy with generalized tonic-clonic seizures alone
4. Progressive myoclonus epilepsies (PME)
5. Autosomal dominant epilepsy with auditory features (ADEAF)
6. Other familial temporal lobe epilepsies E. Less specific age relationship 1. Familial focal epilepsy with variable foci (childhood to adult)
2. Reflex epilepsies

II. DISTINCTIVE CONSTELLATIONS

A. Mesial temporal lobe epilepsy with hippocampal sclerosis (MTLE with HS)

B. Rasmussen syndrome

C. Gelastic seizures with hypothalamic hamartoma

D. Hemiconvulsion-hemiplegia-epilepsy

E. Epilepsies that do not fit into any of these diagnostic categories, distinguished on the basis of 1. Presumed cause (presence or absence of a known structural or metabolic condition)
2. Primary mode of seizure onset (generalized vs. focal)

III. EPILEPSIES ATTRIBUTED TO AND ORGANIZED BY

STRUCTURAL-METABOLIC CAUSES

A. Malformations of cortical development (hemimegalencephaly, heterotopias, etc.)

B. Neurocutaneous syndromes (tuberous sclerosis complex, Sturge-Weber, etc.)

C. Tumor

D. Infection

E. Trauma

IV. ANGIOMA

A. Perinatal insults

B. Stroke

C. Other causes

V. EPILEPSIES OF UNKNOWN CAUSE

VI. CONDITIONS WITH EPILEPTIC SEIZURES NOT TRADITIONALLY DIAGNOSED AS FORMS OF EPILEPSY PER SE

A. Benign neonatal seizures (BNS)

B. Febrile seizures (FS)

Part V of the ILAE classification scheme underscores the fact that the list is far from complete, and that there are still subtypes of epilepsy that have not yet been fully characterized, or that remain unrecognized as distinct syndromes.

Those skilled in the art will recognize that different subtypes of epilepsy are triggered by different stimuli, are controlled by different biological pathways, and have different causes, whether genetic, environmental, and/or due to disease or injury of the brain. In other words, the skilled artisan will recognize that teachings relating to one epileptic subtype are most commonly not necessarily applicable to any other subtype. Of particular importance is the fact that there are a large number of compounds that are used to treat different types of epilepsy, and different epilepsy subtypes respond differently to different anticonvulsant drugs. That is, while a particular drug may be effective against one form of epilepsy, it may be wholly ineffective against others, or even contra-indicated due to exacerbation of symptoms, such as worsening the frequency and severity of the seizures. As a result, efficacy of a particular drug with respect to a particular type of epilepsy is wholly unpredictable, and the discovery that a particular drug is effective in treating in treating a type of epilepsy for which that drug was not previously known to be effective is nearly always surprising, even in cases where the drug is known to be effective against another epilepsy type.

Lennox-Gastaut syndrome (LGS) was first described in 1960, and named for neurologists William G. Lennox (Boston, USA) and Henri Gastaut (Marseille, France). It is a difficult-to-treat form of childhood-onset epilepsy that most often appears between the second and sixth year of life, although it can occur at an earlier or later age. LGS is characterized by frequent seizures and different seizure types; it is typically accompanied by developmental delay and psychological and behavioral problems. In children, common causes of LGS include perinatal brain injury, brain malformations such as tuberous sclerosis or cortical dysplasia, central nervous system (CNS) infection, and degenerative or metabolic disorders of the nervous system.

Daily multiple seizures of different types are typical in LGS. Also typical is the broad range of seizures that can occur. The most common seizure types are tonic-axial, atonic, and absence seizures, but myoclonic, generalized tonic-clonic, and focal seizures can also occur in any LGS patient. Atonic, atypical absence, tonic, focal, and tonic-clonic seizures are also common. Additionally, many LGS patients will have status epilepticus, often of the nonconvulsive type, which is characterized by dizziness, apathy, and unresponsiveness. Further, most patients have atonic seizures, also called drop seizures, which cause their muscles to go limp and result in the patient suddenly and unexpectedly to fall to the ground, often causing significant injury, which is why patients often wear a helmet to prevent head injury.

In addition to daily multiple seizures of various types, children with LGS frequently have arrested/slowed psychomotor development and behavior disorders.

The syndrome is also characterized by a specific finding on electroencephalogram (EEG), specifically an interictal (i.e., between-seizures) slow spike-wave complexes and fast activity during sleep.

Diagnosis

LGS is a syndrome and hence its diagnosis is based on the presence of specific clinical symptoms, signs, and laboratory tests. LGS is typically identified by a triad of features including multiple types of seizures, mental retardation or regression and abnormal EEG with generalized slow spike and wave discharges. Physicians use EEG to assist in diagnosing LGS. Diagnosis may be difficult at the onset of the initial symptom(s) because the triad of features associated with LGS, such as tonic seizures, may not be fully established, and EEG during sleep is required to confirm the condition. Thus, even though there may be overlap in clinical presentation with other epilepsies, LGS is agreed to be a well-defined distinct diagnosis by both the International League Against Epilepsy (ILAE), considered the world's leading expert medical society on epilepsy, and the FDA.

The diagnosis of LGS is more obvious when the patient suffers frequent and manifold seizures, with the classic pattern on the electro-encephalogram (EEG), i.e., a slowed rhythm with Spike-wave-pattern, or with a multifocal and generalizing sharp-slow-wave-discharges at 1.5-2.5 Hz. During sleep, tonic patterns (fast activity) can often be seen.

General medical investigation usually reveals developmental delay and cognitive deficiencies in children with LGS. These may precede development of seizures, or require up to two years after the seizures begin, in order to become apparent.

There may be multiple etiologies for LGS, including genetic, structural, metabolic or unknown. Approximately one-quarter have no prior history of epilepsy, neurological abnormality or developmental delay prior to the onset of LGS symptoms. Underlying pathologies causing LGS may include encephalitis and/or meningitis, brain malformations (e.g., cortical dysplasias), birth injury, hypoxia-ischemia injury, frontal lobe lesions, and trauma.

An important differential diagnosis is 'Pseudo-Lennox-Syndrome', also called atypical benign partial epilepsy of childhood, which differs from LGS, in that there are no tonic seizures; sleeping EEG provides the best basis for distinguishing between the two. In addition, 'Pseudo-Lennox-Syndrome' has an entirely different etiology and prognosis than LGS.

Treatment

The optimum treatment for Lennox-Gastaut syndrome has yet to be established. Many different treatments are currently used in the treatment of this disorder and many more have been tried in the past, most often with little success.

A variety of therapeutic approaches are currently used in LGS, including conventional antiepileptic medications, diet and surgery, however the evidence supporting these therapies is not robust and treatment remains most often ineffective. The use of several common first-line treatments is based on clinical experience or conventional wisdom; examples include broad spectrum anti-convulsant medications, such as valproic acid, and benzodiazepines, most often clonazepam and clobazam. A few drugs have been proven effective for some patients for certain seizure types by double-blind placebo-controlled studies; examples include clobazam, lamotrigine, topiramate, felbamate, and rufinamide, although most patients continue to have significant seizures even while taking these medications. Second-line medications currently in use, such as zonisamide, are prescribed based on results of some open-label uncontrolled studies. The ketogenic diet may be useful in some patients with LGS refractory to medical treatment. Surgical options for LGS include corpus callostomy (for drop attacks), vagus nerve stimulation, and focal cortical resection (in the presence of a single resectable lesion). However, it should be noted that significant improvement from any of these therapies alone or in combination is a rare occurrence.

Despite the severity of LGS's symptoms and the frequency with which it occurs (it accounts for up to 10% of all childhood epilepsies), there is currently no standard evidence-based treatment for the disease. A comprehensive review of the literature [see Hancock E C & Cross J H, Treatment of Lennox-Gastaut syndrome (Review), published in *The Cochrane* Library 2013, Issue 2] discovered only nine randomized controlled trials which evaluated the pharmaceutical treatment of the syndrome. The authors concluded that there is a paucity of research and " . . . that no monotherapy (to date) has been shown to be highly effective in this syndrome." Id at page 12. The authors further concluded that "[t]he optimum treatment for LGS remains uncertain and no study to date has shown any one drug to be highly efficacious". Id at page 12.

There is accordingly a dire and long-felt need to provide an improved method for treating or preventing and/or ameliorating seizures experienced by sufferers of Lennox-Gastaut Syndrome.

SUMMARY OF THE INVENTION

According to a first aspect of the present invention, there is provided a method of treating and/or preventing one or more symptoms of Lennox-Gastaut Syndrome in a patient comprising administering an effective dose to a patient of fenfluramine alone or in combination with one or more drugs as described here.

According to a further aspect of the present invention, there is provided a method of treating, preventing and/or ameliorating seizures in a patient diagnosed with Lennox-Gastaut Syndrome comprising administering an effective dose to a patient of fenfluramine alone or in combination with one or more drugs as described here.

According to a further aspect of the present invention, there is provided a method of treating a patient that exhibits a mutation in one or more of a gene selected from the group consisting of SCN1A, SCN1B, SCN2A, SCN3A, SCN9A, GABRG2, GABRD and PCDH19 by administering to that patient an effective dose of fenfluramine.

A still further aspect of this invention contemplates a method for stimulating one or more 5-HT receptors in the brain of a patient by administering an effective dose of fenfluramine or a pharmaceutically acceptable salt thereof to that patient. Illustrative one or more 5-HT receptors are selected from the group consisting of one or more of 5-$HT_1$, 5-$HT_{1A}$, 5-$HT_{1B}$, 5-$HT_{1C}$, 5-$HT_{1D}$, 5-$HT_{1E}$, 5-$HT_{1F}$, 5-$HT_2$, 5-$HT_{2A}$, 5-$HT_{2B}$, 5-$HT_{2C}$, 5-$HT_3$, 5-$HT_4$, 5-$HT_5$, 5-$HT_{5A}$, 5-$HT_{5B}$ 5-$HT_6$, and 5-$HT_7$. In addition there may be non-5-HT binding in the brain including Sigma, M1 muscarinic, B-adrenergic.

Yet another aspect of the invention contemplates co-administration of an effective dose of one or more co-therapeutic agents with the fenfluramine wherein the co-therapeutic agents can be selected from the group consisting of carbamazepine, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam. Use of a pharmaceutically acceptable salt or base of a co-therapeutic agent is also contemplated.

An aspect of the invention is a method of treating or preventing the symptoms of Lennox-Gastaut syndrome (LGS) in a patient diagnosed with LGS comprising administering an effective dose of fenfluramine or pharmaceutically acceptable salt to the patient, wherein the dose is administered in an amount in the range of from 10.0 mg/kg/day to about 0.01 mg/kg/day, or administered at 120 mg or less; or 60 mg or less or 30 mg or less and may be administered in the absence of the administration of any other pharmaceutically active compound.

In another aspect of the invention, the method is carried out wherein the effective dose is administered in a form selected from the group consisting of oral, injectable, transdermal, buccal, inhaled, nasal, rectal, vaginal, or parental, and wherein the formulation is oral, the formulation may be liquid which may be a solution or a suspension may be present within a container closed with a cap connected to a syringe graduated to determine the volume extracted from the container wherein the volume extracted relates to the amount of fenfluramine in a given liquid volume of formulation e.g. one millimeter of formulation contains 2.5 mg of fenfluramine. In another aspect of the invention, the method is administered in a solid oral formulation in the form of a tablet, capsule, lozenge, or sachet.

The method may be carried out as a co treatment with a different pharmaceutically active compound. The method may be carried out in a process wherein the patient is first then subjected to a series of tests to confirm diagnoses of LGS.

Another aspect of the invention is a kit for treating Lennox-Gastaut syndrome (LGS) in a patient diagnosed with LGS wherein the kit comprises a formulation comprising a pharmaceutically acceptable carrier and an active ingredient comprising fenfluramine and instructions for treating a patient diagnosed with LGS by administering the formulation to the patient. In yet another aspect, wherein the fenfluramine is in an oral liquid or a solid oral dosage form or a transdermal patch; and the kit further comprises instructions for treating a patient diagnosed with LGS by administering the formulation to the patient.

In another aspect of the invention, the kit consists of an oral liquid formulation in a container and a syringe with instructions, wherein the concentration of the fenfluramine in the liquid is calibrated based on calibrations on the syringe and includes calibrations wherein a milliliter of solution equates to a known amount of fenfluramine such as 0.1 mg, 0.2 mg etc., to 1.0 mg.

In another aspect of the invention, the kit includes instructions relating to dosing the patient based on patient weight and volume of solution based on the concentration of fenfluramine in the solution.

Another aspect of the invention is a use of a fenfluramine composition in treating and or preventing symptoms of Lennox-Gastaut syndrome (LGS) and a patient diagnosed with LGS which use may include placing the fenfluramine in a liquid solution and withdrawing that liquid solution into a graduated syringe.

These and other objects, advantages, and features of the invention will become apparent to those persons skilled in the art upon reading the details of the methods of treating symptoms of Lennox-Gastaut Syndrome as more fully described below.

BRIEF DESCRIPTION OF THE DRAWINGS

The present disclosure is best understood from the following detailed description when read in conjunction with the accompanying drawings. Included in the drawings are the following figures.

FIG. 1 is a table summarizing the procedures followed during each of the patient visits which are conducted over the course of the clinical trial described in Example 1.

DETAILED DESCRIPTION OF THE INVENTION

Figure 2:
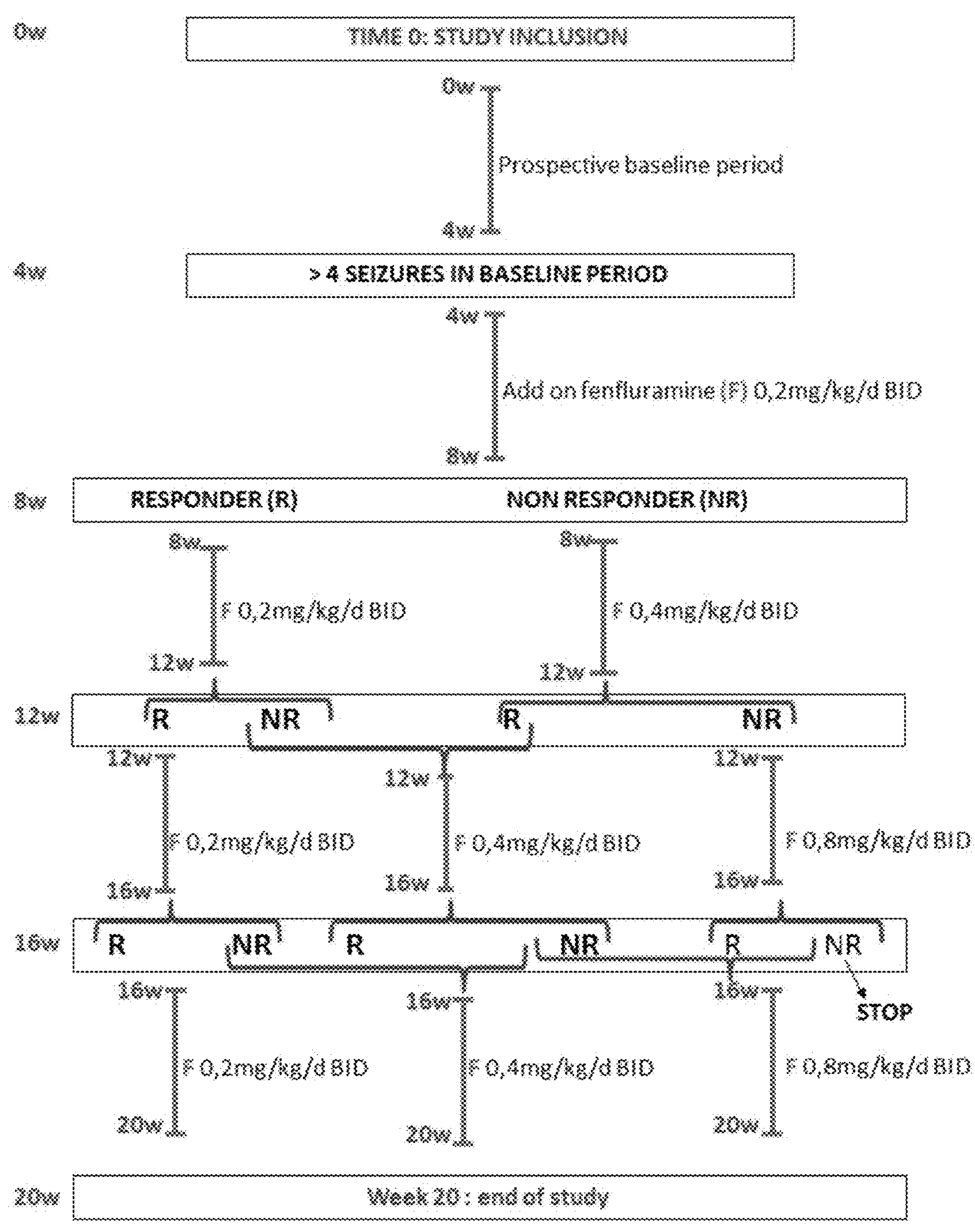
FIG. 2 is a flow chart illustrating the manner in which fenfluramine dosages are increased for non-responding patients over the course of the clinical trial.

Before the present method, kits and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms “a”, “an”, and “the” include plural referents unless the context clearly dictates otherwise. Thus, for example, reference to “a seizure” includes a plurality of such seizures and reference to “the formulation” includes reference to one or more formulations and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

After extensive research, it has unexpectedly been found that fenfluramine can be used to treat, or at least minimize the effects of Lennox-Gastaut Syndrome.

To avoid doubt, the term "prevention" of seizures means the total or partial prevention (inhibition) of seizures. Ideally, the methods of the present invention result in a total prevention of seizures. However, the invention also encompasses methods in which the instances of seizures are decreased in frequency by at least 40%, at least 50%, at least 55%, at least 60%, at least 65%, at least 70%, at least 75%, at least 80%, at least 85%, or at least 90%. In addition, the invention also encompasses methods in which the instances of seizures are decreased in duration or severity by at least 40%, at least 50%, at least 55%, at least 60%, at least 65%, at least 70%, at least 75%, at least 80%, at least 85%, or at least 90%.

Without being bound by theory, fenfluramine has been known to trigger the release of serotonin (5-HT) in the brain due to disruption of its vesicular storage and to inhibit serotonin reuptake. However, until the present invention was made, it was not known that fenfluramine's mechanism of action made it suitable for the treatment of Lennox-Gastaut syndrome (LGS). In fact, there are no scientific publications demonstrating or even hypothesizing that 5-HT abnormalities are a possible underlying pathophysiologic cause for LGS or are causally related to the associated seizures in this specific epilepsy condition. Furthermore, since there has been no scientific hypothesis relating serotonin abnormalities in LGS, there are no studies nor even individual case reports in the medical literature which describe attempts to treat LGS using medications that interacts with serotonin. The lack of data or even speculation in the literature regarding the use of fenfluramine or serotonergic agents in general to treat LGS are facts that strongly support the unexpected nature of this invention: given that LGS is a devastating refractory epilepsy condition and the number of people affected, investigators would be strongly motivated to investigate any treatment they perceived as having any potential for efficacy.

Thus, according to a still further aspect of the present invention, there is provided a method of stimulating one or more 5-HT receptors in the brain of a patient by administering an effective dose of fenfluramine to said patient, said one or more 5-HT receptors being selected from one or more of $5\text{-HT}_1$, $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$ $5\text{-HT}_6$, and $5\text{-HT}_7$ amongst others. In certain embodiments of this aspect of the invention, the patient has been diagnosed with Lennox-Gastaut Syndrome.

In embodiments of the invention, any effective dose of fenfluramine can be employed. However, surprisingly low doses of fenfluramine have been found by the inventors to be effective, particularly for inhibiting or eliminating seizures in Lennox-Gastaut Syndrome patients.

DOSE BY WEIGHT (MG/KG/DAY) Thus in some cases, in a preferred embodiment of the invention, a daily dose of less than about 10 mg/kg/day, such as less than about 10 mg/kg/day, less than about 9 mg/kg/day, less than about 8 mg/kg/day, less than about 7 mg/kg/day, less than about 6 mg/kg/day, less than about 5 mg/kg/day, less than about 4 mg/kg/day, less than about 3.0 mg/kg/day, less than about 2.5 mg/kg/day, less than about 2.0 mg/kg/day, less than about 1.5 mg/kg/day, less than about 1.0 mg/kg/day, such as about 1.0 mg/kg/day, about 0.95 mg/kg/day, about 0.9 meg/kg/day, about 0.85 mg/kg/day, about 0.85 mg/kg/day, about 0.8 mg/kg/day, about 0.75 mg/kg/day, about 0.7 mg/kg/day, about 0.65 mg/kg/day, about 0.6 mg/kg/day, about 0.55 mg/kg/day, about 0.5 mg/kg/day, about 0.45 mg/kg/day, about 0.4 mg/kg/day, about 0.350 mg/kg/day, about 0.3 mg/kg/day, about 0.25 mg/kg/day, about 0.2 mg/kg/day, about 0.15 mg/kg/day to about 0.1 mg/kg/day, about 0.075 mg/kg/day, about 0.05 mg/kg/day, about 0.025 mg/kg/day, about 0.0225 mg/kg/day, about 0.02 mg/kg/day, about 0.0175 mg/kg/day, about 0.015 mg/kg/day, about 0.0125 mg/kg/day, or about 0.01 mg/kg/day is employed.

Put differently, a preferred dose is less than about 10 to about 0.01 mg/kg/day. In some cases the dose is less than about 10.0 mg/kg/day to about 0.01 mg/kg/day, such as less than about 5.0 mg/kg/day to about 0.01 mg/kg/day, less than about 4.5 mg/kg/day to about 0.01 mg/kg/day, less than about 4.0 mg/kg/day to about 0.01 mg/kg/day, less than about 3.5 mg/kg/day to about 0.01 mg/kg/day, less than about 3.0 mg/kg/day to about 0.01 mg/kg/day, less than about 2.5 mg/kg/day to about 0.01 mg/kg/day, less than about 2.0 mg/kg/day to about 0.01 mg/kg/day, less than about 1.5 mg/kg/day to about 0.01 mg/kg/day, or less than about 1.0 mg/kg/day to 0.01 mg/kg/day, such as less than about 0.9 mg/kg/day, less than about 0.8 mg/kg/day, less than about less than about 0.7 mg/kg/day, less than about 0.6 mg/kg/day to about 0.01 mg/kg/day, less than about 0.5 mg/kg/day to about 0.01 mg/kg/day, less than about 0.4 mg/kg/day to about 0.01 mg/kg/day, less than about 0.3 mg/kg/day to about 0.01 mg/kg/day, or less than about 0.2 mg/kg/day to about 0.01 mg/kg/day.

As indicated above the dosing is based on the weight of the patient. However, for convenience the dosing amounts may be preset such as in the amount of 1.0 mg, 2.5 mg, 5 mg, 10 mg, 15 mg, 20 mg, 30 mg, 40 mg, or 50 mg. In certain instances, the dosing amount may be preset such as in the amount of about 0.25 mg to about 5 mg, such as about 0.25 mg, about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5.0 mg.

In general the smallest dose which is effective should be used for the particular patient.

The dosing amounts described herein may be administered one or more times daily to provide for a daily dosing amount, such as once daily, twice daily, three times daily, or four or more times daily, etc.

In certain embodiments, the dosing amount is a daily dose of 30 mg or less, such as 30 mg, about 29 mg, about 28 mg, about 27 mg, about 26 mg, about 25 mg, about 24 mg, about 23 mg, about 22 mg, about 21 mg, about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, or about 1 mg. In general the smallest dose which is effective should be used for the particular patient. In some cases, the dose is generally well below the dosing used in weight loss.

ROUTES OF ADMINISTRATION The dose of fenfluramine administered according to the methods of the present invention can be administered systemically or locally. Methods of administration may include administration via enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, it may be desirable to administer one or more compounds of the invention locally to the area in need of treatment. This may be achieved, for example, by local infusion during, topical application, by injection, by means of a catheter, by means of a suppository, or by means of an implant, said implant being of a porous, non-porous, or gelatinous material, including membranes, such as sialastic membranes, or fibers.

DOSAGE FORMS/ROUTE OF ADMIN The dose of fenfluramine administered in the methods of the present invention can be formulated in any pharmaceutically acceptable dosage form including, but not limited to (a) oral dosage forms such as tablets including orally disintegrating tablets, capsules, and lozenges, oral solutions or syrups, oral emulsions, oral gels, oral films, buccal liquids, powder e.g. for suspension, and the like; (b) injectable dosage forms; (c) transdermal dosage forms such as transdermal patches, ointments, creams; (c) inhaled dosage forms; and/or (e) nasally, (f) rectally, (g) vaginally administered dosage forms.

DOSGE FORM/FREQUENCY OF ADMIN Such dosage forms can be formulated for once a day administration, or for multiple daily administrations (e.g. 2, 3 or 4 times a day administration). Alternatively, for convenience, dosage forms can be formulated for less frequent administration (e.g., monthly, bi-weekly, weekly, every fourth day, every third day, or every second day), and formulations which facilitate extended release are known in the art.

DOSAGE FORMS/PREPARATION, COMPONENTS The dosage form of fenfluramine employed in the methods of the present invention can be prepared by combining fenfluramine or a pharmaceutically acceptable salt thereof with one or more pharmaceutically acceptable diluents, carriers, adjuvants, and the like in a manner known to those skilled in the art of pharmaceutical formulation.

ORAL DOSAGE FORMS/SUITABLE FORMULATION TYPES & COMPONENTS THEREOF In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient (fenfluramine), as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

ORAL DOSAGE FORMS/EXCIPIENTS, For an oral solid pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers.

By way of illustration, the fenfluramine composition can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Particular formulations of the invention are in an oral liquid form. The liquid can be a solution or suspension and may be an oral solution or syrup, which is included in a bottle with a syringe graduated in terms of milligram amounts which will be obtained in a given volume of solution. The liquid solution makes it possible to adjust the volume of solution for appropriate dosing of small children, who can be administered fenfluramine in an amount anywhere from 1.25 mg to 30 mg and any amount between in 0.25 milligram, increments and thus administered in amounts of 1.25 mg, 1.5 mg, 1.75 mg, 2.0 mg, etc.

A specific aspect of the invention is a treatment carried out to relieve symptoms of Lennox-Gastaut by the administration of only fenfluramine. However, the fenfluramine may be co-administered with other known pharmaceutical drugs such as a co-therapeutic agent selected from the group consisting of carbamazepine, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam and a pharmaceutically acceptable salt or base thereof.

The co-therapeutic agents have recommended dosing amounts. Those recommended dosing amounts are provided within the most current version of the Physician's Desk Reference (PDR) or http://emedicine.medscape.com/ both of which are incorporated herein by reference specifically with respect to the co-therapeutic agents listed above and more specifically with respect to the dosing amounts recommended for those drugs.

In connection with the present invention, the co-therapeutic agent can be used in the recommended dosing amount or can be used in a range of from $100^{th}$ to 100 times 1/10 to 10 times 1/5 to 5 times 1/2 to twice the recommended dosing amount or any incremental 1/10 amount in between those ranges.

As a specific example of a combination of co-therapeutic agents with fenfluramine, the co-therapeutic agent may be any one of or all three of stiripentol, clobazam, and valproate. The fenfluramine may be administered in the amount of 0.8 mg/kg of patient body weight and co-administered with 3500 mg of stiripentol, 20 mg of clobazam, and 25 mg per kg of valproate. Each of those amounts may be increased to twice, three times, five times, or ten times that amount or decreased by 10%, 50%, or 75%.

An aspect of the invention includes a kit for treating and or preventing symptoms of LGS in a patient diagnosed with LGS, the kit comprising:

a container holding a liquid formulation of fenfluramine;
a dispensing device connected to the container and configured to withdraw the liquid formulation from the container;
instructions for administering the liquid formulation to a patient in order to treat LGS.

In alternate embodiments, the dispensing device may be a syringe or graduated pipette useful for delivering varying doses of the fenfluramine liquid. In another embodiment, the dispensing device is a metered dosing device capable of dispensing a fixed volume of fenfluramine liquid. In one exemplary embodiment, the dose delivered by the metered dosing device is adjustable.

The formulation may be a solution or suspension and is prepared such that a given volume of the formulation contains a known amount of active fenfluramine.

For example, in one embodiment of this aspect, the dispensing device is a syringe is graduated in one millimeter increments and the liquid fenfluramine formulation is characterized such that one millimeter in volume of formulation includes precisely one milligram of fenfluramine. In this manner, the patient may be correctly dosed with a desired milligram dosage of fenfluramine based on a volume of liquid formulation administered to the patient orally.

In alternate embodiments, the dispenser is a syringe connected to the container and configured to withdraw the liquid formulation from the container, wherein the syringe is marked with levels of graduation noting volume of formulation withdrawn, or a metered dose dispenser for delivering a predetermined volume of the formulation to said patient, or a metered dispensing device calibrated to deliver a predetermined volume of the liquid, permitting convenient, consistent, and accurate dosing.

In a method of the present invention, fenfluramine can be employed as a monotherapy in the treatment of Lennox-Gastaut Syndrome. Alternatively, fenfluramine can be co-administered in combination with one or more pharmaceutically active agents, which may be provided together with the fenfluramine in a single dosage formulation, or separately, in one or more separate pharmaceutical dosage formulations. Where separate dosage formulations are used, the subject composition and ore or more additional agents can be administered concurrently, or at separately staggered times, i.e., sequentially.

In one embodiment, the agents are co-therapeutic agents, such as anticonvulsants. Preferred co-therapeutic agents can be selected from the group consisting of carbamazepine, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam. Use of a pharmaceutically acceptable salt of a co-therapeutic agent is also contemplated.

Fenfluramine can be administered in the form of the free base, or in the form of a pharmaceutically acceptable salt, for example selected from the group consisting of hydrochloride, hydrobromide, hydroiodide, maleate, sulphate, tartrate, acetate, citrate, tosylate, succinate, mesylate and besylate. Further illustrative pharmaceutically acceptable salts can be found in Berge et al., J. Pharm Sci. (1977) 68(1): 1-19.

Fenfluramine for use in the methods of the present invention may be produced according to any pharmaceutically acceptable process known to those skilled in the art. Examples of processes for synthesizing fenfluramine are provided in the following documents: GB1413070, GB1413078 and EP441160.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents.

A method of the present invention can be practiced on any appropriately diagnosed patient. In alternate exemplary embodiments of the present invention, the patient is aged about 18 or less, about 16 or less, about 14 or less, about 12 or less, about 10 or less, about 8 or less, about 6 or less or about 4 or less to about 0 months or more, about 1 month or more, about 2 months or more, about 4 months or more, about 6 months or more or about 1 year or more. Thus, in this embodiment, the diagnosed patient is about one month old to about 18 years old when treated.

The invention is further illustrated in the following Examples.

EXAMPLE 1

Add-on Therapy with Low Dose Fenfluramine (FFA) in Lennox-Gastaut

The efficacy of fenfluramine as an add-on treatments in Lennox-Gastaut patients is studied in a Phase 2 Clinical Trial. The study protocol is described and preliminary results are presented here.

Trial Objectives and Design

An open-label, non-placebo controlled add-on study was designed to assess the efficacy and safety of low-dose add-on fenfluramine across a range of fenfluramine doses (0.2, 0.4, 0.8 mg/kg/day, to a maximum of 30 mg/day). The trial was conducted over a 20 week period, with responders eligible for follow-on treatment, with follow-up appointments at three month intervals.

Inclusion and Exclusion Criteria

Patients were recruited from childhood epilepsy clinics in Leuven and Antwerp, Belgium, and selected for inclusion in the study according to criteria comprising a combination of age, physical and psychological characteristics, and resistance to treatment with conventional therapies. Details of selection criteria are provided below.

| | |
|---|---|
| MINIMUM REQUIREMENTS: | Multiple seizure types; |
| Electro-clinical epilepsy syndrome compatible with Lennox-Gastaut syndrome | Tonic seizures present in all cases |
| | EEG showing slow spike saves and abnormal background |
| | Abnormal cognitive development |
| | MRI compatible with Lennox-Gastaut epilepsy (including no progressive disease) |
| Drug Resistant Seizures | Patients received at least two anti-epileptic drugs (AEDs), including VNS, during the 4 week period prior to inclusion |
| | Eligible seizure types |
| | Tonic-clonic (GTC) - REQUIRED |
| | Tonic (TS) |
| | Atonic (AS) |
| | Clearly recognizable focal (FS) |
| | At least 4 documented seizures during 4 week period prior to inclusion |
| | Minimum of 4 seizures in at least 2 separate weeks |
| Age | Between 3 and 18 years |

Once enrolled, subjects are removed from the study in cases of serious adverse events, non-compliance, or lack of efficacy. Treatment is also stopped in the event of increased severity and frequency of seizures after discussion with the principle investigator; cardiac abnormalities (specifically, valvular problems), and/or adverse events (specifically, SAE, SAR or SUSAR) after discussion with the principle investigator. Patients may also withdraw voluntarily. Upon withdrawing, a safety examination (i.e., blood sampling and cardiac ultrasound) is performed and fenfluramine use is tapered for one week at 50% of end dosage and then withdrawn completely.

Trial Protocol

Study duration is 20 weeks, ending at week 20 after inclusion of 20 patients, i.e., 20 weeks following the enrollment of the $20^{th}$ patient. Patients who respond to treatment are enrolled in a follow-on study and assessed on an ongoing basis.

Patients are examined during six clinical visits (V1 through V6) scheduled at four week intervals, ending with V6 at week 20. Thereafter, responders continue in a follow-up study, with visits scheduled every three months. At each visit, endpoints and safety criteria are assessed, and dosages adjusted as necessary.

During the study period, patients are prohibited from receiving certain medications and foods: (1) felbamate is prohibited as a concomitant medication unless the following criteria are met: the patient has been treated for at least 18 months prior to screening; has stable liver function and hematology laboratory tests, and the dose is expected to remain constant throughout the study; (2) dugs that interact with central serotonin, including imipramine, monoamine oxidase inhibitors, SSRIs, SNRIs, or vortioxetine; and (3) drugs or foods that potentially interact with fenfluramine via the CYP-2D6, CYPD-3A4, and/or CYP-2B6 pathways, except for pre-approved short-term use where required by medical necessity. Pregnancy testing, use of birth control, and breast feeding restrictions were also required during the study period and for the duration of subsequent fenfluramine treatment.

An abbreviated trial flowchart appears in Table 1, shown in FIG. 1. At V1, inclusion and exclusion criteria are assessed, clinical diagnosis confirmed, and the following information is collected: baseline demographics, pre-baseline seizure counts, current treatment regimens (both AEDs and VNS), and sleep quality. In addition, safety blood samples are collected, blood levels of anti-epileptic drugs ("AEDs") are determined, and cardiac function is evaluated using ultrasound imaging and EKG traces. Urine pregnancy tests in female subjects of childbearing potential are also done, and the patient's quality of life is assessed by means of clinical global impressions (both parents and physician) and sleep quality. Patients meeting entry criteria are enrolled and begin a prospective baseline period.

Add-on treatment is begun at V2. Participants being receiving an initial fenfluramine dose of 0.2 mg/kg/day. Endpoints and safety criteria are assessed (seizure counting, adverse effects, pregnancy testing, and quality of life indicators (CGI, sleep scale)). Additional safety blood samples, AED blood levels and cardiac evaluation are done only if clinically indicated. A seizure diary and medication are dispensed.

At each of V3-V5, endpoints and safety criteria are again assessed. Dosages of non-responders are adjusted according to trial protocol. A schema for dose escalation is shown in FIG. 2.

At V6, endpoints and safety criteria are again assessed. Safety blood samples, AED blood levels and cardiac evaluation are repeated. Responders may enter the follow-up study. Non-responders begin FFA tapering, receiving 50% of the end dosage for 1 week and then discontinuing treatment.

Follow-Up Study:

Responders at 20 weeks continue in a follow-up study, with visits scheduled at 3 month intervals. Patients receive a starting dose equal to the dosage received at week 20. At each visit, endpoints and safety criteria are assessed (seizure counting, current treatment, adverse effects, quality of life indicators (CGI, sleep scale)), pregnancy testing is performed, safety blood samples are collected, blood level AEDs are determined and cardiac function is evaluated using EKG and cardiac ultrasound. Dosages may be increased as necessary, up to a maximum of 30 mg/day. Follow up ends when fenfluramine becomes available as a regular treatment or at the election of the patient and/or treating physician if serious side effects occur and/or the drug is no longer effective.

Materials and Methods

Ethics and regulatory approvals: Trial conduct complies with the most recent version of the principles of the Declaration of Helsinki, the principles of GCP, and in accordance with all applicable regulatory requirements. The study protocol and related documents is subject to ethical review by all requisite authorities. Participants have given written informed consent prior to their enrollment and participation in compliance with all applicable laws, regulations and ethical guidelines as required, and ICFs are retained at participating trial sites in accordance with all applicable regulatory agencies and laws. All information and data related to the Study and disclosed to the Participating Site and/or Study Investigator are treated as confidential and will not be disclosed to third parties or used for any purpose other than the performance of the study. Data collection, processing and disclosure of personal data is subject to compliance with applicable personal data protections and personal data processing requirements.

Fenfluramine: Oral fenfluramine solution (2.5 mg/ml or 5 mg/ml) is provided by Zogenix Pharma. Starting dosage is 0.2 mg/kg/day BID; second step at 0.4 mg/kg/day BID; maximum dosage at 0.8 mg/kg/day BID or 30 mg/day BID, whichever is less. The drug is dispensed by Zogenix Pharma. Labeled bottles containing the oral fenfluramine suspension is given to patients and controlled at each visit. Bottle labels are kept in individual patient files. Calculation of bottle number and control of labels are done at the trial's conclusion. Patient compliance is assessed by control of oral solution quantity at each visit and collection of seizure diary with notification of drug intake.

Concomitant treatment: Lennox-Gastaut patients participating in the study receive concomitant treatment with two or more anti-epileptic drugs commonly used in the treatment of the disorder. The drug regimen is unchanged during baseline (the period from V1 to V2) and the full trial period (V2 to V6).

Laboratory tests: Blood analysis and urine pregnancy tests are done in central lab at UZ Leuven. Safety blood samples are tested for hemogram, electrolytes, liver function (SGOT, SGPT, LDH, PT) and kidney function (urea, creatinine)). AED blood level determination is limited to phenytoin, phenobarbital, carbamazepine, and valproate.

Safety assessment: Treatment safety is assessed using a combination of physical examination, blood testing, cardiac evaluation, and adverse event reporting. With respect to adverse event reporting, reporting is not required for expected AEs, moderate weight loss and decrease of appetite with no significant weight loss (<P3).

Data Handling and Statistical Analysis: Data is coded and is protected from disclosure outside of research teams according to the terms of the research protocol and the informed consent document. Subjects' names or other identifiers must be stored separately ("site file") from their research data and replaced with a unique code to create a new identify for the subject. Coded data are not anonymous. Data is collected in standardized CRF.

A priori data on possible efficacy is unavailable. Sample size is set at 20. The study is not randomized. Descriptive analysis of outcome parameters is done at weeks 8, 12, 16 and 20. All included subjects are counted for analysis. Reasons for withdrawal are documented.

Interim Results

At the time results were reported, a total of 13 patients had been recruited and 12 enrolled. 9 patients were receiving treatment; 3 others were within the baseline period (V1 to V2).

None of the 9 patients receiving fenfluramine reported serious side effects. 3 patients receiving 0.2 mg/kg/day showed significant decreases in total seizure frequency.

The early interim data suggests that low-dose fenfluramine used as an add-on treatment is effective in reducing seizure frequency in Lennox-Gastaut patients.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating seizures associated with Lennox-Gastaut syndrome (LGS) in a patient suffering from LGS, comprising:

administering an oral dose of fenfluramine or a pharmaceutically acceptable salt thereof to the patient in an amount in a range of 0.2 mg/kg/day to 0.8 mg/kg/day up to a maximum of 30 mg/day.

2. The method of claim 1, wherein the oral dose is a liquid formulation.

3. The method of claim 2, wherein the oral dose consists essentially of fenfluramine or a pharmaceutically acceptable salt thereof as the active ingredient.

4. The method of claim 1, further comprising administering a co-therapeutic agent selected from the group consisting of carbamazepine, ethosuximide, fosphenytoin, lamotrigine, levetiracetam, phenobarbital, progabide, topiramate, stiripentol, valproic acid, verapamil, clobazam, clonazepam, diazepam, ethyl loflazepate, lorazepam, midazolam and a pharmaceutically acceptable salt thereof.

5. The method of claim 1, wherein the instances of seizures are reduced in frequency as compared to the patient suffering from LGS without an oral dose of fenfluramine, or a pharmaceutically acceptable salt thereof.

6. The method of claim 1, wherein the instances of seizures are reduced in duration as compared to the patient suffering from LGS without an oral dose of fenfluramine, or a pharmaceutically acceptable salt thereof.

7. The method of claim 1, wherein the instances of seizures are reduced in severity as compared to the patient suffering from LGS without an oral dose of fenfluramine, or a pharmaceutically acceptable salt thereof.

8. The method of claim 1, wherein the oral dose of fenfluramine, or a pharmaceutically acceptable salt thereof, is administered daily for two or more days.

9. The method of claim 1, wherein the oral dose of fenfluramine, or a pharmaceutically acceptable salt thereof, is administered daily for at least one week.

10. The method of claim 1, wherein the oral dose of fenfluramine, or a pharmaceutically acceptable salt thereof, is administered daily for at least four weeks.

11. The method of claim 1, wherein prior to the treatment, the Lennox-Gastaut syndrome (LGS) patient is refractory to conventional antiepileptic medications.

12. A method of treating seizures associated with Lennox-Gastaut syndrome (LGS) in a patient suffering from LGS, comprising:

administering an oral solution of fenfluramine or a pharmaceutically acceptable salt thereof to the patient in an amount in a range of 0.2 mg/kg/day to 0.8 mg/kg/day up to a maximum of 30 mg/day; and administering a drug selected from the group consisting of stiripentol, clobazam, valproate and combinations thereof.

13. The method of claim 12, wherein the oral dose of fenfluramine, or a pharmaceutically acceptable salt thereof, is administered daily for two or more days.

14. The method of claim 12, wherein the oral dose of fenfluramine, or a pharmaceutically acceptable salt thereof, is administered daily for at least one week.

15. A method of treating seizures associated with Lennox-Gastaut syndrome (LGS) in a patient suffering from LGS, comprising:

administering an oral dose of fenfluramine or a pharmaceutically acceptable salt thereof to the patient in an amount in a range of 0.2 mg/kg/day to 0.8 mg/kg/day up to a maximum of 30 mg/day; and administering a therapeutically effective amount of stiripentol to the patient.

16. The method of claim 15, wherein the oral dose of fenfluramine is in a liquid formulation.

17. The method of claim 15, wherein the oral dose of fenfluramine, or a pharmaceutically acceptable salt thereof, is administered in a divided dose twice daily for two or more days.

18. The method of claim 15, wherein the oral dose of fenfluramine, or a pharmaceutically acceptable salt thereof, is administered daily for at least one week.

19. The method of claim 1, further comprising diagnosing the patient as having Lennox-Gastaut syndrome (LGS) based on the presence of specific clinical symptoms, signs, and findings on an electroencephalogram (EEG) of the patient prior to administering the oral dose of fenfluramine or a pharmaceutically acceptable salt thereof.

20. The method of claim 1, wherein the seizures are selected from the group consisting of tonic-axial seizures, atonic (drop) seizures, absence seizures, myoclonic seizures, generalized tonic-clonic seizures, and focal seizures.

* * * * *